United States Patent [19]

Vidaluc et al.

[11] Patent Number: 5,288,758

[45] Date of Patent: Feb. 22, 1994

[54] UREA DERIVATIVES, THEIR PREPARATION AND THEIR APPLICATION IN THERAPY

[75] Inventors: Jean-Louis Vidaluc; Dennis Bigg, both of Castres, France

[73] Assignee: Pierre Fabre Medicament, Boulogne, France

[21] Appl. No.: 918,424

[22] Filed: Jul. 22, 1992

[30] Foreign Application Priority Data

Jul. 25, 1991 [FR] France .................. 91 09446

[51] Int. Cl.$^5$ .................. A01N 47/30; C07C 275/04
[52] U.S. Cl. .................. 514/597; 514/353; 514/357; 514/584; 514/587; 514/594; 514/595; 546/305; 564/23; 564/28; 564/44; 564/50; 564/56; 552/289
[58] Field of Search .................. 564/26, 48, 50, 54, 564/59, 22, 27, 28, 29, 38, 52, 53, 57, 60, 23; 552/289; 546/305; 514/580, 584, 585, 586, 587, 591, 596, 597, 598, 588, 353, 357

[56] References Cited

U.S. PATENT DOCUMENTS

| | | | |
|---|---|---|---|
| 3,049,562 | 8/1962 | Wright, Jr. et al. | 260/553 |
| 3,061,640 | 10/1962 | Beaver et al. | 260/552 |
| 3,903,154 | 9/1975 | Singer | 260/553 A |
| 4,297,373 | 10/1981 | Sulkowski et al. | 424/322 |
| 4,474,707 | 10/1984 | Sulkowski et al. | 260/456 |
| 5,015,644 | 5/1991 | Roth et al. | 514/247 |
| 5,106,873 | 4/1992 | O'Brien et al. | 514/596 |
| 5,116,848 | 5/1992 | Trivedi | 514/332 |

*Primary Examiner*—Glennon H. Hollrah
*Assistant Examiner*—Brian M. Burn

*Attorney, Agent, or Firm*—Dressler, Goldsmith, Shore & Milnamow

[57] ABSTRACT

New urea derivatives corresponding to the general formula 1

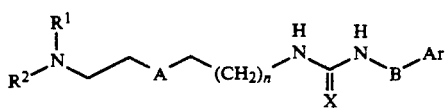

in which:

$R^1$ represents a $C_1$–$C_4$ alkyl group;

$R^2$ represents:
- a $C_5$–$C_7$ cycloalkyl group
- a cycloalkylmethyl group in which the cycloalkyl radical contains from 5 to 7 carbon atoms
- a benzyl group
- a benzyl group in which the aromatic ring bears a $C_1$–$C_4$ alkyl group, a $C_1$–$C_4$ alkoxy group, a halogen atom or a nitro group;

A represents an oxygen atom or a methylene radical;

n represents 1 or 2;

X represents an oxygen or sulfur atom;

B represents a direct bond, a methylene radical or a carbonyl radical;

as well as the therapeutically acceptable salts of these molecules.

The invention also relates to the application of the compounds of general formula 1 in therapy, and to the preparation processes.

7 Claims, No Drawings

UREA DERIVATIVES, THEIR PREPARATION AND THEIR APPLICATION IN THERAPY

The present invention, carried out at the Pierre Fabre Research Center, relates to new urea derivatives, to their preparation and to their application in therapy.

The compounds of the invention correspond to the general formula 1:

$$R^2\text{-}N(R^1)\text{-}CH_2\text{-}CH_2\text{-}A\text{-}(CH_2)_n\text{-}NH\text{-}C(=X)\text{-}NH\text{-}B\text{-}Ar \quad \quad 1$$

in which:

$R^1$ represents a $C_1$–$C_4$ alkyl group;

$R^2$ represents:
- a $C_5$–$C_7$ cycloalkyl group
- a cycloalkylmethyl group in which the cycloalkyl radical contains from 5 to 7 carbon atoms
- a benzyl group
- a benzyl group in which the aromatic ring bears a $C_1$–$C_4$ alkyl group, a $C_1$–$C_4$ alkoxy group, a halogen atom or a nitro group;

A represents an oxygen atom or a methylene radical;

n represents 1 or 2;

X represents an oxygen or sulfur atom;

B represents a direct bond, a methylene radical or a carbonyl radical;

Ar represents:
- a pyridyl group
- a phenyl group of formula:

(phenyl ring substituted by $R^3$ and $R^4$)

where $R_3$ and $R_4$, independently of one another, represent a hydrogen atom, a halogen atom, a nitro group, a $C_1$–$C_4$ alkyl group, a $C_1$–$C_4$ alkoxy group, a phenyl group or a trifluoromethoxy group;

an oxofluorenyl group of formula:

(fluorenone structure)

a dioxoanthracenyl group of formula:

(anthraquinone structure)

a naphthyl group.

The invention also covers the salts of the compounds of general formula 1 with pharmaceutically acceptable inorganic or organic acids. Among pharmaceutically acceptable acids, hydrochloric acid or fumaric acid may be mentioned by way of example.

The compounds of general formula 1 of the invention may be prepared according to the following reaction scheme:

$$R^2\text{-}N(R^1)\text{-}CH_2\text{-}CH_2\text{-}A\text{-}(CH_2)_n\text{-}NH_2 \quad \quad 2$$
$$+$$
$$Ar\text{-}B\text{-}N=C=X \quad \quad 3$$
$$\longrightarrow$$
$$R^2\text{-}N(R^1)\text{-}CH_2\text{-}CH_2\text{-}A\text{-}(CH_2)_n\text{-}NH\text{-}C(=X)\text{-}NH\text{-}B\text{-}Ar \quad \quad 1$$

where $R^1$, $R^2$, A, n, B, X and Ar are defined as above.

The starting amines 2 and the heterocumulenes of formula 3 must be prepared according to conventional methods.

When X represents a sulfur atom, the reacton of an amine of general formula 2 with a compound of general formula 3 may be performed at a temperature ranging from room temperature to the refluxing temperature of the solvent.

The solvent employed can be, by way of example, a chlorinated solvent such as dichloromethane or dichloroethane, a ketonic solvent such as acetone, an alcoholic solvent, for example ethanol, or an ether such as tetrahydrofuran.

When X represents an oxygen atom, the reaction between an amine of general formula 2 and an isocyanate of general formula 3 may be performed at a temperature of between 0° C. and 35° C. in an aprotic solvent. The solvent employed can be, by way of example, acetone, toluene, a chlorinated solvent such as dichloromethane or dichloroethane or an ether such as tetrahydrofuran.

The salts of the compounds of the invention may be obtained from a solution of the free base by adding a solution of an acid such as fumaric acid, maleic acid or hydrochloric acid in a suitable solvent such as ethanol. Precipitation of the salt may be facilitated by adding a solvent such as ether or ethyl acetate.

The examples which follow illustrate the invention without, however, limiting its scope.

The analyses and the IR and NMR spectra confirm the structure of the compounds obtained according to the invention.

Example 1

1-Benzyl-3-{2-[2-(N-cyclohexyl-N-ethylamino)ethoxy]-ethyl}urea:

Compound No. 2; $R^1$=Et, $R^2$=cyclohexyl, A=O, n=1, X=O, B=$CH_2$, Ar=$C_6H_5$.

0.7 ml of benzylisocyanate is added to 10 ml of dichloromethane and the solution is cooled using an ice bath. A solution of 1.2 g of 2-[2-(N-cyclohexyl-N-ethylamino)ethoxy]ethylamine in 5 ml of dichloromethane is added with stirring.

The reaction mixture is allowed to return to room temperature and, after 18 hours, the solvent is evaporated off. The oily brown residue is purified by chromatography on silica gel, eluted with an ethyl acetate/methanol (50:50) mixture. An oil is obtained, which crystallizes in hexane. After filtration and drying under vacuum, 1.0 g of the compound 2 is obtained in the form of pale beige crystals.

M.p.: 66°-67° C.

Example 2

1-Benzoyl-3-[5-(N-cyclohexylmethyl-N-methylamino)-pentyl]thiourea:

Compound No. 5; $R^1$=Me, $R^2$=cyclohexylmethyl, A=$CH_2$, n=1, X=S, B=CO, Ar=$C_6H_5$.

0.25 ml of benzoyl isothiocyanate is added to a solution of 0.4 g of 5-(N-cyclohexylmethyl-N-methylamino)pentylamine in 10 ml of dichloromethane. After one night with stirring at room temperature, the solvent is evaporated off under reduced pressure. The orange-colored oil obtained is purified by chromatography on silica gel, eluted with chloroform/methanol (95:5). After evaporation, 0.6 g of an orange-colored oil is recovered, which is treated with an ethanolic solution of fumaric acid and ether to obtain 0.55 g of the fumarate of the compound 5 in the form of white crystals.

M.p.: 103°-4° C.

Example 3

1-{2-[2-(N-Benzyl-N-methylamino)ethoxy]ethyl}-3-(α-naphthyl)thiourea:

Compound No. 7; $R^1$=Me, $R^2$=$C_6H_5CH_2$, A=O, n=1, X=S, B=direct bond, Ar=α-naphthyl.

A solution of 1.85 g of naphthyl isothiocyanate in 30 ml of dichloromethane is added to 2.08 g of 2-[2-(N-benzyl-N-methylamino)ethoxy]ethylamine, and the mixture is stirred at room temperature for 16 hours. The solvent is evaporated off, and the pale yellow oil obtained crystallizes. The solid is taken up with isopropylether and, after filtration and drying, 2.85 g of the compound 6 are obtained in the form of white crystals.

M.p.: 116°-117° C.

Example 4

1-Benzoyl-3-{3-[2-(N-benzyl-N-methylamino)ethoxy]-propyl}-thiourea:

Compound No. 8; $R^1$=Me, $R^2$=$C_6H_5CH_2$, A=O, n=2, X=S, B=CO, Ar=$C_6H_5$.

1.4 ml of benzoyl isothiocyanate are added to a solution of 2.22 g of 3-[2-(N-benzyl-N-methylamino)-ethoxy]propylamine in 20 ml of absolute ethanol. The mixture is brought to reflux for 1 hour and the solvent is evaporated off under reduced pressure. The oily residue obtained is purified by chromatography on silica gel, eluted with chloroform. 1.1 g of a pale yellow oil are obtained, which is treated with an ethanolic solution of fumaric acid and ether to give 0.7 g of the fumarate of the compound 8 in the form of white crystals.

M.p.: 97°-100° C.

Table 1 below summarizes the main products synthesized, which illustrate the invention without, however, limiting its scope.

TABLE 1

| Comp. No. | $R^1$ | $R^2$ | A | n | X | B | Ar | Salt/Base | M.p. (°C.) |
|---|---|---|---|---|---|---|---|---|---|
| 1 | Me | $C_6H_5CH_2$ | O | 1 | O | d.b.* | 4-$NO_2.C_6H_4$ | HCl | 176-7 |
| 2 | Et | c.$C_6H_{11}$ | O | 1 | O | $CH_2$ | $C_6H_5$ | Base | 66-7 |
| 3** | Me | $C_6H_5CH_2$ | O | 1 | O | CO | $C_6H_5$ | Base | Oil |
| 4 | Me | $C_6H_5CH_2$ | $CH_2$ | 1 | S | CO | $C_6H_5$ | ½ (Fumarate) | 140-2 |
| 5 | Me | c.$C_6H_{11}CH_2$ | $CH_2$ | 1 | S | CO | $C_6H_5$ | Fumarate | 103-4 |
| 6 | Me | $C_6H_5CH_2$ | O | 1 | S | d.b. | 4-$Cl.C_6H_4$ | HCl | 133-5 |
| 7 | Me | $C_6H_5CH_2$ | O | 1 | S | d.b. | α-naphthyl | Base | 116-7 |
| 8 | Me | $C_6H_5CH_2$ | O | 2 | S | CO | $C_6H_5$ | Fumarate | 97-100 |
| 9 | Me | $C_6H_5CH_2$ | O | 1 | S | CO | $C_6H_5$ | HCl | 116-18 |
| 10 | Me | $C_6H_5CH_2$ | O | 1 | S | CO | 4-$Me.C_6H_4$ | Fumarate | 152-3 |
| 11 | Me | $C_6H_5CH_2$ | O | 1 | S | CO | 4-$MeO.C_6H_4$ | HCl | 140-2 |
| 12 | Me | $C_6H_5CH_2$ | O | 1 | S | CO | 4-$Cl.C_6H_4$ | Fumarate | 149-51 |
| 13 | Me | $C_6H_5CH_2$ | O | 1 | S | CO | 3-$NO_2.C_6H_4$ | Fumarate | 94-6 |
| 14 | Me | $C_6H_5CH_2$ | O | 1 | S | CO | 3.4-$Cl_2.C_6H_3$ | Fumarate | 119-21 |
| 15 | Me | $C_6H_5CH_2$ | O | 1 | S | CO | 4-$Ph.c_6H_4$ | HCl | 130-2 |
| 16 | Me | $C_6H_5CH_2$ | O | 1 | S | CO | β-Naphthyl | HCl | 202-4 |
| 17 | Me | $C_6H_5CH_2$ | O | 1 | S | CO | (fluorenone-2-yl) | HCl | 205-10 |
| 18 | Me | $C_6H_5CH_2$ | O | 1 | S | CO | (anthraquinon-2-yl) | Base | 113-5 |
| 19 | Me | c.$C_6H_{11}$ | O | 1 | S | CO | $C_6H_5$ | ½ (Fumarate) | 140-2 |
| 20 | Me | 3-$NO_2.C_6H_4CH_2$ | O | 1 | S | d.b. | 3-Pyridyl | Fumarate | 70-90 |
| 21 | Me | $C_6H_5CH_2$ | O | 1 | S | d.b. | 4-$CF_3O.C_6H_4$ | HCl | 142-3 |
| 22 | Me | 3-$NO_2.C_6H_4CH_2$ | O | 1 | S | d.b. | 3.4-$(MeO)_2.C_6H_3$ | HCl | 118-25 |

*Direct bond
**IR(KBr): 1680 $cm^{-1}$. NMR($CDCl_3$/TMS): δ (multiplicity, number of protons): 2.27(s.3H): 2.66(t.2H): 3.62(m.8H): 7.36(m.5H): 7.50(m.3H): 8.02(m.2H): 9.06(t.1H): 10.13(s.1H).

The compounds of the invention were subjected to pharmacological tests which showed their value as acetylcholinesterase inhibitors.

To this end, the compounds were studied according to the method described by G.L. Ellman et al., *Biochem. Pharmacol.* 7, 88–95 (1961).

The results obtained on some compounds of the invention are recorded, by way of example, in Table 2.

TABLE 2

| Inhibition of acetylcholinesterase activity | |
|---|---|
| Compound No. | IC$_{50}$ (nM) |
| 5 | 50 |
| 11 | 26 |
| 12 | 30 |
| 13 | 15 |
| 14 | 55 |
| 16 | 100 |
| Tacrine | 120 |

The compounds of the invention are acetylcholinesterase inhibitors; they may thus be useful in the treatment of diseases such as myasthenia, memory disorders and dementia such as senile dementia or Alzheimer's disease.

Pharmaceutical preparations containing these active principles may be formulated for oral, rectal, parenteral or local administration, for example in the form of capsules, tablets, granules, hard gelatin capsules, liquid solutions, syrups or suspensions to be swallowed, and may contain the appropriate excipients.

It is also possible to combine other pharmaceutically and therapeutically acceptable active principles therewith.

I claim:

1. A urea derivative corresponding to the general formula

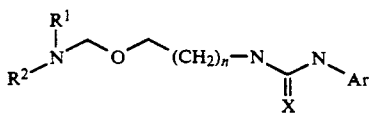

or

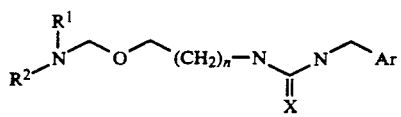

or

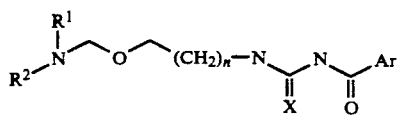

or

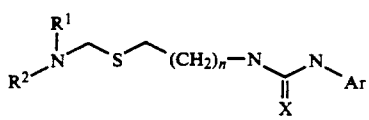

or

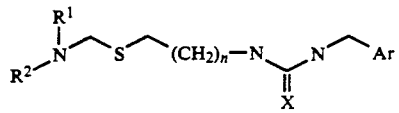

or

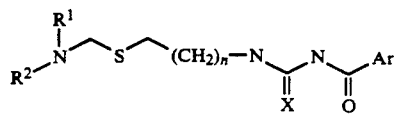

in which:
R$^1$ represents a C$_1$–C$_4$ alkyl group;
R$^2$ represents:
  a C$_5$–C$_7$ cycloalkyl group
  a cycloalkylmethyl group in which the cycloalkyl radical contains from 5 to 7 carbon atoms
  a benzyl group
  a benzyl group in which the aromatic ring bears a C$_1$–C$_4$ alkyl group, a C$_1$–C$_4$ alkoxy group, a halogen atom or a nitro group;
n represents 1 or 2;
X represents an oxygen or sulfur atom;
Ar represents:
  a pyridyl group
  a phenyl group of formula:

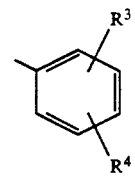

where R$_3$ and R$_4$, independently of one another, represent a hydrogen atom, a halogen atom, a nitro goup, a C$_1$–C$_4$ alkyl group, a C$_1$–C$_4$ alkoxy group, a phenyl group or a trifluoromethoxy group;
an oxofluorenyl group of formula:

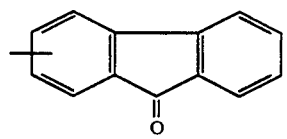

a dioxoanthracenyl group of formula:

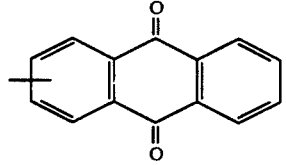

a naphthyl group, as well as the therapeutically acceptable organic or inorganic salts of this molecule.

2. A compound as claimed in claim 1, which is chosen from:
- 1-{2-[2-(N-Benzyl-N-methylamino)ethoxy]ethyl}-3-(4-nitrophenyl)urea
- 1-Benzyl-3-{2-[2-(N-cyclohexyl-N-ethylamino)ethoxy]-ethyl}urea

- 1-Benzoyl-3-{2-[2-(N-benzyl-N-methylamino)ethoxy]ethyl}urea
- 1-Benzoyl-3-[5-(N-benzyl-N-methylamino)pentyl]thiourea
- 1-Benzoyl-3-[5-(N-cyclohexylmethyl-N-methylamino)-pentyl]thiourea
- 1-{2-[2-(N-Benzyl-N-methylamino)ethoxy]ethyl}-3-(4-chlorophenyl)thiourea
- 1-{2-[2-(N-Benzyl-N-methylamino)ethoxy]ethyl}-3-(α-naphthyl)thiourea
- 1-Benzoyl-3-{3-[2-(N-benzyl-N-methylamino)ethoxy]propyl}thiourea
- 1-Benzoyl-3-{2-[2-(N-benzyl-N-methylamino)ethoxy]ethyl}thiourea
- 1-{2-[2-(N-Benzyl-N-methylamino)ethoxy]ethyl}-3-(4-methylbenzoyl)thiourea
- 1-{2-[2-(N-Benzyl-N-methylamino)ethoxy]ethyl}-3-(4-methoxybenzoyl)thiourea
- 1-{2-[2-(N-Benzyl-N-methylamino)ethoxy]ethyl}-3-(4-chlorobenzoyl)thiourea
- 1-{2-[2-(N-Benzyl-N-methylamino)ethoxy]ethyl}-3-(3-nitrobenzoyl)thiourea
- 1-{2-[2-(N-Benzyl-N-methylamino)ethoxy]ethyl}-3-(3,4-dichlorobenzoyl)thiourea
- 1-{2-[2-(N-Benzyl-N-methylamino)ethoxy]ethyl}-3-(4-phenylbenzoyl)thiourea
- 1-{2-[2-(N-Benzyl-N-methylamino)ethoxy]ethyl}-3-(β-naphthoyl)thiourea
- 1-{2-[2-(N-Benzyl-N-methylamino)ethoxy]ethyl}-3-(9-oxo-2-fluorenoyl)thiourea
- 1-{2-[2-(N-Benzyl-N-methylamino)ethoxy]ethyl}-3-(9,10-dioxo-2-anthracenoyl)thiourea
- 1-Benzoyl-3-{2-[2-(N-cyclohexyl-N-methylamino)ethoxy]-ethyl}thiourea
- 1-[2-{2-[N-Methyl-N-(m-nitrobenzyl)amino]ethoxy}ethyl]-3-(3-pyridyl)thiourea
- 1-{2-[2-(N-Benzyl-N-methylamino)ethoxy]ethyl}-3-(4-trifluoromethoxyphenyl)thiourea
- 1(3,4-Dimethoxyphenyl)-3-[2-{2-[N-methyl-N-(m-nitrobenzyl)amino]ethoxy}ethyl]thiourea 3. A pharmaceutical composition, which contains a compound defined according to claim 1.

4. A pharmaceutical composition, which contains a compound defined according to claim 2.

5. The compound as claimed in claim 1, wherein X represents a sulfur atom.

6. The compound as claimed in claim 1, wherein $R_2$ represents a benzyl group.

7. The method of treating a patient suffering from below normal transmission of cholinergic nervous impulses which comprises administering to said patient a compound according to claim 1 in an amount effective to inhibit acetylcholinesterase in said patient.

* * * * *